United States Patent
Sepetka et al.

[11] Patent Number: 5,911,728
[45] Date of Patent: Jun. 15, 1999

[54] CANNULA PURSE STRING SUTURE CLAMPING DEVICE

[75] Inventors: Ivan Sepetka, Los Altos; Robert C. Glines, Cameron Park; Dwight P. Morejohn, Davis; Edmund J. Morrissey, III, Aptos, all of Calif.

[73] Assignee: Cardiothoracic Systems, Inc., Cupertino, Calif.

[21] Appl. No.: 08/972,797

[22] Filed: Nov. 18, 1997

[51] Int. Cl.$^6$ .................................................. A61B 17/04
[52] U.S. Cl. .......................................... 606/151; 606/139
[58] Field of Search ...................... 606/151, 139, 606/157, 158

[56] References Cited

U.S. PATENT DOCUMENTS

| | | | |
|---|---|---|---|
| 5,188,636 | 2/1993 | Fedotov | 606/144 |
| 5,382,260 | 1/1995 | Dormandy, Jr. et al. | 606/151 |
| 5,490,856 | 2/1996 | Person et al. | 606/139 |
| 5,649,938 | 7/1997 | Allen et al. | 606/144 |
| 5,683,405 | 11/1997 | Yacoubian et al. | 606/158 |
| 5,722,982 | 3/1998 | Ferreira et al. | 606/151 |
| 5,792,154 | 8/1998 | Doan et al. | 606/151 |

*Primary Examiner*—Gary Jackson
*Attorney, Agent, or Firm*—Lyon & Lyon LLP

[57] ABSTRACT

Several embodiments of a clamping device are disclosed, for tightening and securing a purse string suture used to seal the tissue around a cannula or a catheter or the like placed in a heart, major vessel or other tissue structure. The clamping device includes a compressible sleeve means solidly secured at a proximal end to a compression-applying means such as a clamp mechanism. A suture-pulling needle is inserted through a common lumen, whereby the trailing ends of the suture thread which forms the purse string suture may be pulled through the compressible sleeve means and clamp mechanism. Application of a force to the clamp mechanism while it is not locked to the trailing ends compresses the compressible sleeve means. Release of the clamp mechanism locks the enclosed trailing ends of the suture thread. The compressed sleeve means applies constant and precalibrated tension on the purse string suture to continuously maintain the seal about the cannula. The clamping device is removed by unlocking the clamp mechanism and withdrawing the device from the suture thread.

23 Claims, 4 Drawing Sheets

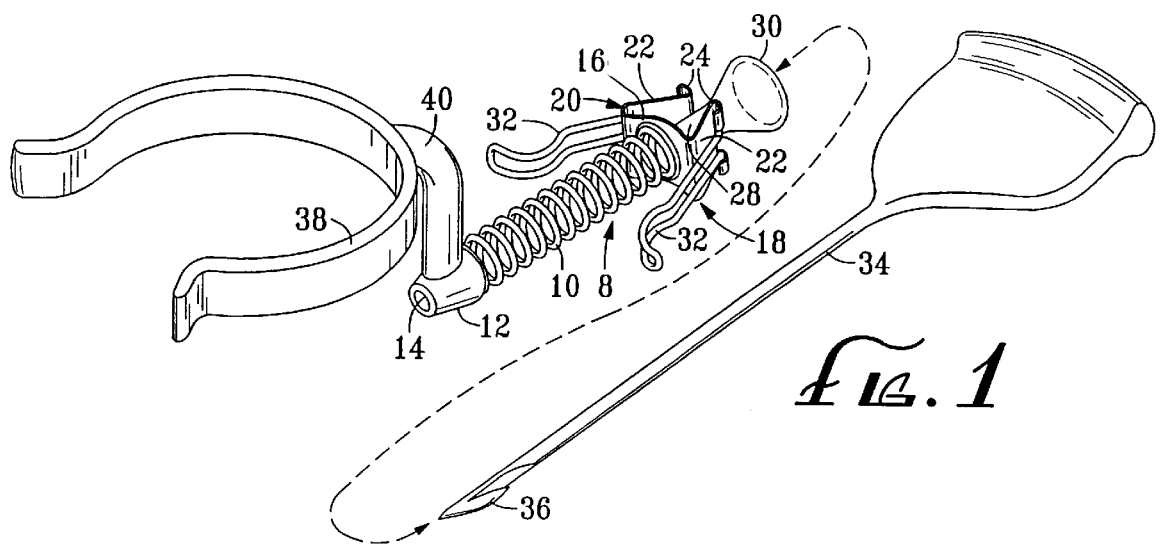
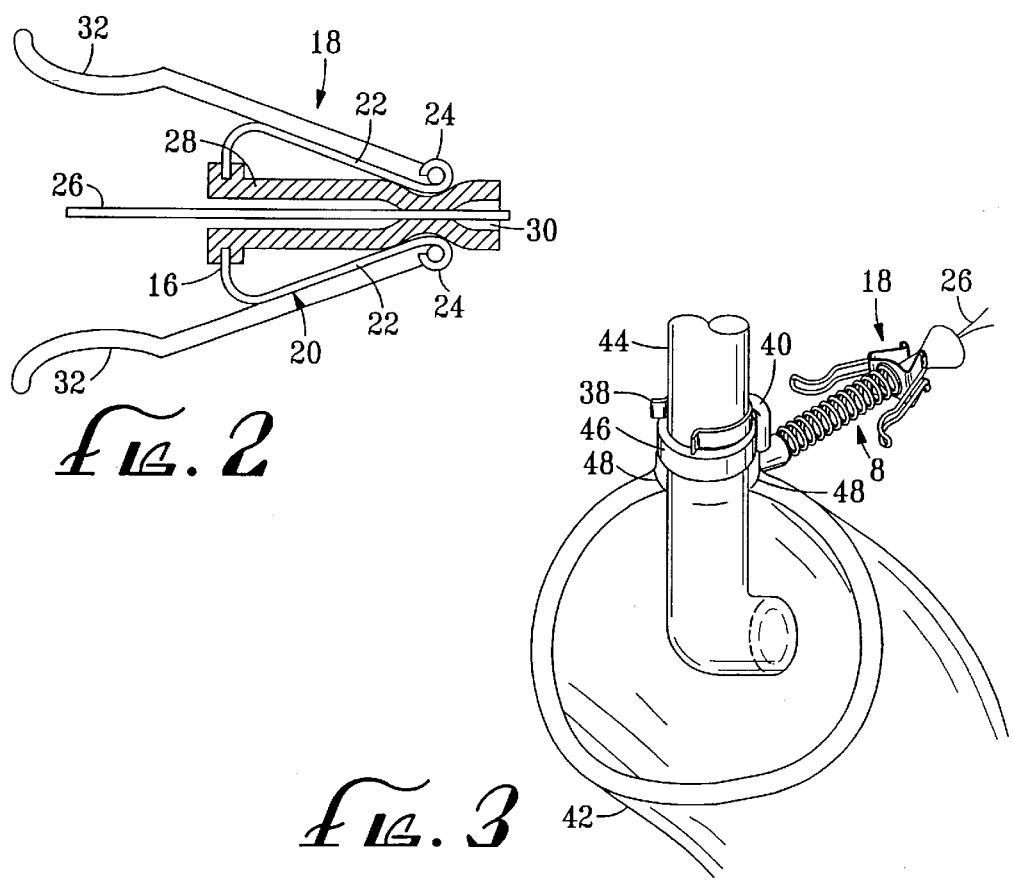

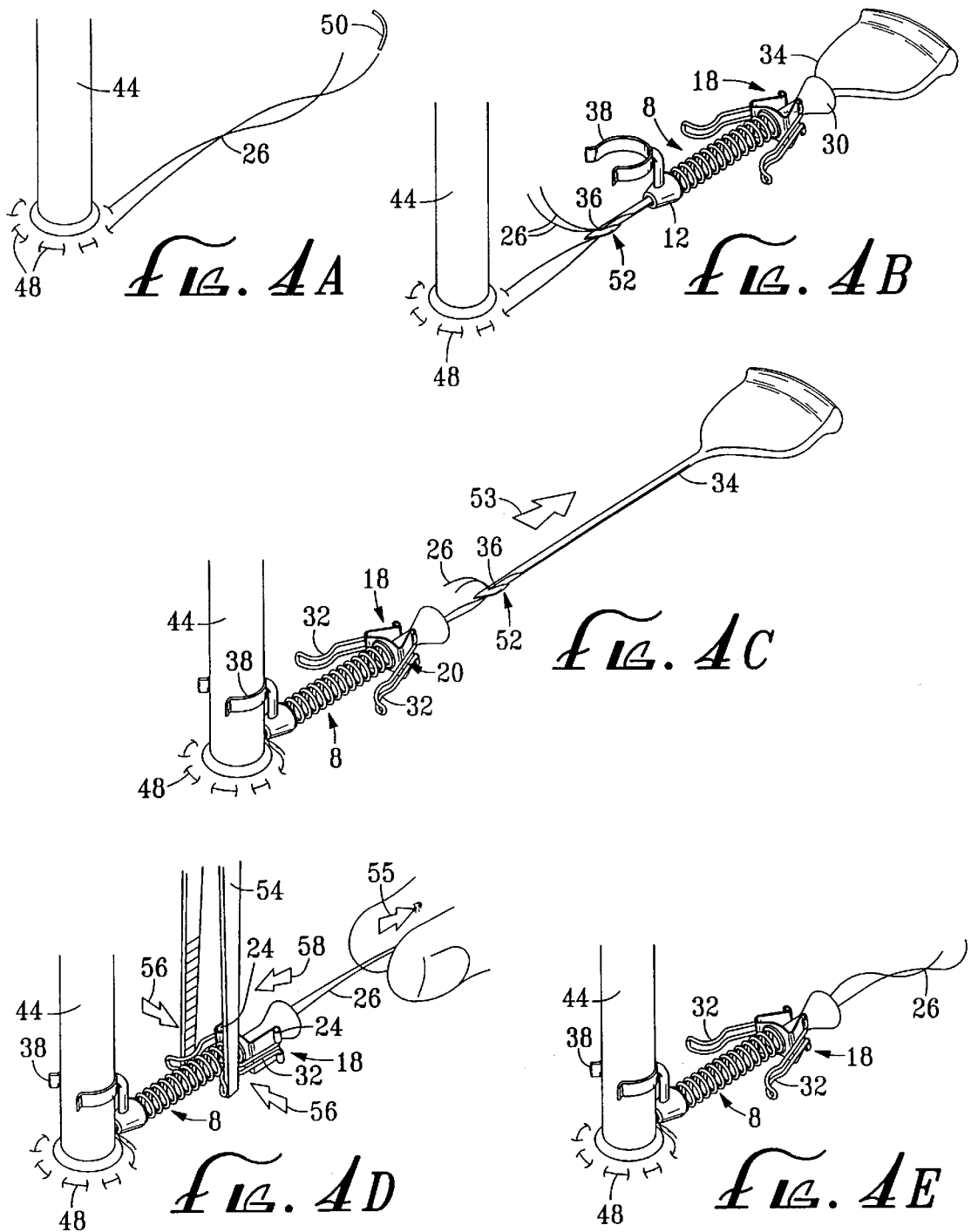

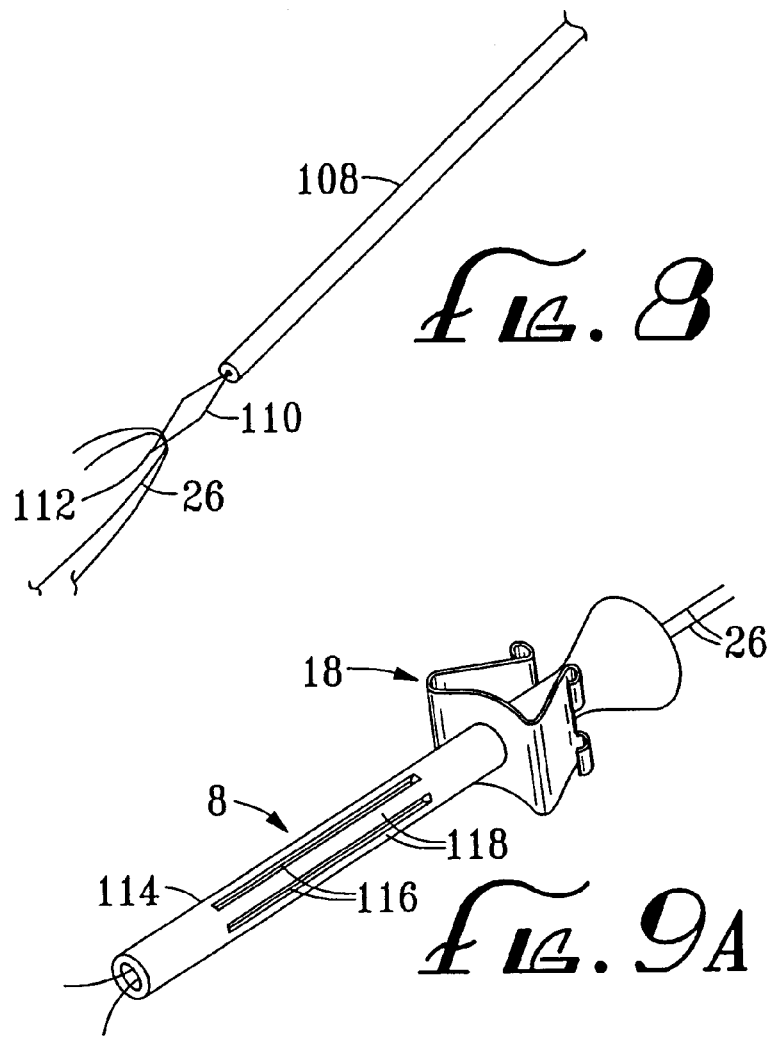

CANNULA PURSE STRING SUTURE CLAMPING DEVICE

FIELD OF THE INVENTION

The present invention relates generally to a cardiopulmonary bypass (CPB) surgical procedure in which a cannula (or cannulae) is placed in the heart and/or in a major vein to provide for blood bypass to a heart-lung machine and, more particularly, to a clamping device and installation procedure for detachably securing the trailing ends of a suture of a purse string suture used to seal the cannula in place in the heart or major vessels.

BACKGROUND OF THE INVENTION

Purse string sutures frequently are used in surgical procedures such as in cardiac surgeries wherein the heart, major arteries, and/or major veins are cannulated for cardiopulmonary bypass (CPB). More specifically, a purse string suture is used to seal the tissue around a cannula, a catheter, or the like, placed within the cardiac tissue.

Accordingly, a cardiopulmonary bypass procedure requires a cannula (or cannulae) to be placed into the right side of the heart (typically the right atrium) or in the major veins (typically the superior vena cava and/or inferior vena cava) to drain blood from the patient and deliver it to a pump-oxygenator, commonly known as the heart-lung machine, and then return the oxygenated blood to the body through a perfusion cannula. In some circumstances, the perfusion cannula may be placed into a large peripheral artery, such as the common femoral artery, however it generally is more acceptable to return the blood through a cannula placed directly into the ascending aorta.

The insertion of the arterial (aortic) perfusion cannula include the procedures of entering the patient's chest and placing two concentric purse string sutures into the anterior wall of the ascending aorta just proximal to upstream of the brachiocephalic trunk. The diameter of the purse string sutures are made large enough to accommodate the size of the aortic perfusion cannula, which are dictated by individual patient physiology. The cannula is inserted through a small incision made through the wall of the aorta into its lumen in the center of the purse string sutures. Typically the trailing ends of the respective suture threads then are each threaded through a "choker" tube or sleeve, sometimes referred to as a Romell tourniquet, which act as a tourniquet for tightening and securing the purse string sutures about the cannula. The purse string sutures are tightened by means of their respective choker tubes, and a suitable clamp such as a forceps is used to lock the trailing ends of the sutures within the choker tubes. The tightened and clamped purse string sutures seal the aortic wall around the perfusion cannula in order to prevent the escape of blood from, or the introduction of air into, the aorta. The venous drainage cannula(e) is similarly inserted directly through an incision centered within a single purse string suture into the right atrium of the heart or into the superior and/or inferior vena cavae, for connection to the drainage side of the pump-oxygenator. The cardiopulmonary bypass is instituted by allowing unoxygenated blood which is returning to the right side of the heart to be diverted into the pump-oxygenator where it is oxygenated and temperature-adjusted, and then pumped into the patient's arterial system via the aortic perfusion cannula.

In the construction of the purse string sutures, typically two concentric rows, with off-setting or staggered stitches and with each row having 4 to 5 stitches, are placed for the arterial perfusion cannula. Because the blood flow pressure is greater on the arterial side of the heart, a double purse string suture is used as a precaution in case one suture breaks. Two rows of stitches also help to minimize the risk of blood leakage from the incision site. On the other hand, because there are not the pressure concerns on the venous side, only a single purse string suture having about 5 to 6 stitches typically is used for venous cannulation. As the cardioplegia cannula is in a portion of the circulatory system that has been bypassed by CPB, there is virtually no concern of blood leakage, and only a single purse string suture is necessary to seal the tissue around the cannula and hold it in place. Examples of methods and apparatus for constructing purse string sutures are described in copending U.S. patent application Ser. No. 08/850,321, filed May 2, 1997, and entitled, Automatic Purse String Suture Device, which application is incorporated herein by reference.

Conventionally, purse string sutures are manually stitched by the surgeon or are applied by a surgical instrument such as those disclosed in the above mentioned patent application. In laparoscopic surgery, for example, where tubular ends of tissue are being tied off, the entire thickness of the tissue wall may be penetrated to achieve the desired suturing. However, in cardiac surgery, and particularly in the context of aortic cannulation, total penetration of the aortic wall by the purse string suture can cause catastrophic effects and thus, the surgeon must be cautious so as not to penetrate the entire thickness of the vessel wall.

As previously mentioned, up to the present time purse string sutures have been tightened and locked in place using tourniquets comprised of lengths of choker tubes to draw the trailing ends of the suture thread tight, and locking forceps to clamp the trailing ends within the tubes to lock the purse string suture. It follows that generally there are from three to five purse string sutures placed about two to four cannulae, thereby resulting in as many cannulae, choker tubes, and forceps within the surgical opening in which a surgeon is operating. The existence of these additional auxiliary instruments, though cumbersome, can be tolerated in a median sternotomy construction where the chest is fully opened and a relatively large surgical opening is provided. However, this is not the case in a minimally invasive construction such as a mini-thoracotomy or mini-sternotomy where the space within a surgical opening is very restricted. Thus, the use of the high profile choker tubes and forceps to secure the purse string sutures in place about the cannulae is highly disadvantageous since such auxiliary instruments obstruct the surgeon's ready access to the surgical site. With the progression towards less invasive cardiac surgical techniques which require the visualization and manipulation of surgical instruments through less invasive openings in the chest, there is a need for compact surgical instruments, particularly auxiliary instruments, to improve upon the space which is available to a surgeon for viewing the surgical site as well as for accommodating the surgeon's hands.

Another objective of less invasive surgeries is to reduce the time a patient is subjected to potentially traumatic procedures, such as the necessary clamping of the aorta prior to implementing CPB and thereby reduce the interruption in systemic circulation. Likewise, it is desirable to reduce the amount of time it takes to perform the more menial tasks during, for example, placing a cannula, such as tightening and securing the purse string sutures, and for subsequently removing the purse string sutures after the completion of surgery.

Accordingly, it would be highly desirable to provide a choking or clamping device for tightening and securing a purse string suture about a cannula and the like, wherein the clamping device is small and unobtrusive, is readily applied and removed and thus is optimally adapted to minimally invasive surgical procedures. In addition, it would be desirable for the clamping device to continuously provide a constant, predetermined tension to a purse string suture.

SUMMARY OF THE INVENTION

The present invention provides a cannula purse string clamping device and method of installation which circumvents the problems of typical purse string securing devices while lending itself particularly to minimally invasive surgical constructions. To this end, the clamping device of the invention includes a compressible sleeve means such as, for example, a compression spring, a compressible tube or lumen formed of an elastomeric material, nitinal, etc., secured at one end to a selected compression-applying clamp mechanism. The unitary compressible sleeve means and clamp mechanism includes an axially extending lumen therethrough whereby an elongate suture-pulling needle may be inserted through the lumen. The needle includes a suture-engaging hook, snare, etc., on its distal end whereby, in the installation, the trailing ends of the suture which forms the purse string suture are drawn through the lumen in the sleeve means and clamp mechanism. The clamp mechanism includes selected grips which, when pressed together, open the clamp to allow the ends of the suture to be pulled through the clamping device. Additional pulling on the trailing ends against the unlocked clamp mechanism compresses the compressible sleeve means while forcing the distal end thereof against the cannula, causing the purse string suture to cinch tightly around the aorta wall tissue and the cannula. The grips are released to secure the trailing ends of the suture in the clamp mechanism and thus to lock the clamping device in place. The compressible sleeve means parameters are selected to allow the sleeve means to apply relatively constant, continuous, and precalibrated tension on the purse string suture to continuously and firmly seal the encompassed tissue about the cannula.

The present invention thus provides as an object and advantage, a low profile purse string choking or clamping device which does not obstruct the view or activities of a surgeon.

Another object and advantage of the present invention is to provide a readily installed tightening and choking or clamping device for a purse string suture utilizing a removable suture-pulling needle and a surgeon's conventional forceps.

A further object and advantage of the present invention is to apply relatively constant, continuous, and precalibrated tension to a purse string suture to maintain an optimal seal of the purse string suture about the cannula.

These and other objects and advantages of the present invention will be more fully understood and appreciated by reference to the drawings and the following description of the invention.

BRIEF DESCRIPTION OF THE DRAWINGS

FIG. 1 is a perspective view of an embodiment of the present invention clamping device, including means for installing the invention.

FIG. 2 is a cross-sectional view of the clamp mechanism of FIG. 1.

FIG. 3 is a perspective view of the invention secured to a purse string suture used to seal a cannula in place in, for example, an aorta.

FIGS. 4A–4E are perspective views illustrating several steps for installing the clamping device of the present invention in conjunction with a cannula utilizing a purse string suture.

FIG. 8 is a perspective view illustrating an alternative means for hooking the suture thread at the tip of the suture-pulling needle of FIG. 1.

FIGS. 9A and 9B are perspective views illustrating an alternative embodiment of the compressible sleeve means of FIGS. 1, 4A–4E and 5, in an uncompressed and compressed state, respectively.

DETAILED DESCRIPTION OF THE INVENTION

Figure 5:
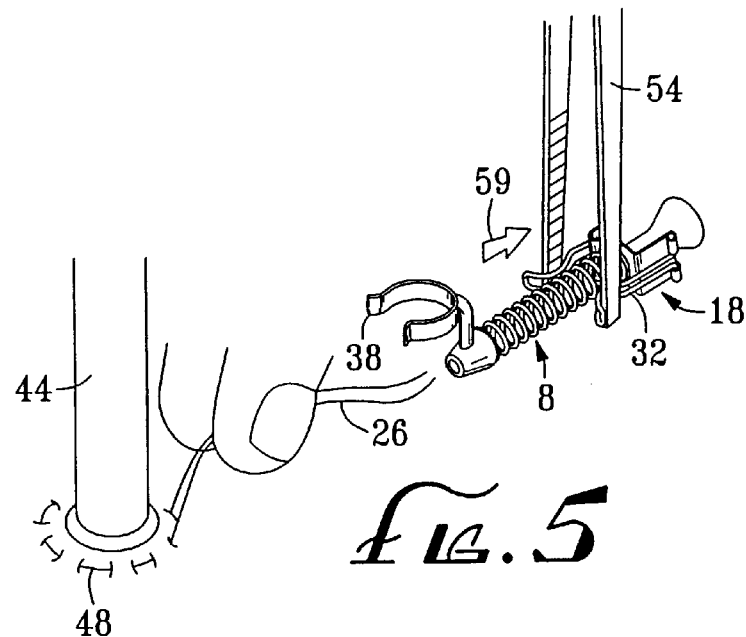
FIG. 5 is a perspective view illustrating a procedure for removing the device of the invention from operative attachment to a cannula utilizing a purse string suture.

Various preferred and exemplary embodiments of the cannula purse string clamping device of the present invention and the method of installation thereof are described in further detail with reference to the figures. Similar reference numbers are used throughout the figures for like elements or components of the invention. For purposes of description, the present invention is described in the context of the application of purse string sutures to the cardiac vasculature for purposes of cannulation. This specific application is intended for purposes of example only, and it is understood that those skilled in the relevant art will appreciate that the present invention has application in other surgical procedures. For example, the clamping device of the invention may be used for securing a catheter and the like in place in a tissue structure.

FIG. 1 illustrates an embodiment of the clamping device of the invention which includes a compressible sleeve means 8 comprised in this embodiment of an elongate compression spring 10 of selected length, diameter and strength. By way of example only, the spring 10 may have a length of one-half to two inches in an uncompressed state. The inside diameter may be about 0.05 to about 0.3 inch (or about 0.13 to about 0.76 cm). A distal end of the spring 10 has a generally cylindrical cap 12 solidly secured thereto with an axial purse spring suture port 14 therein. The proximal end of the spring 10 has solidly secured thereto a base portion 16 of a clamp mechanism 18. Referring also to FIG. 2, the clamp mechanism 18 of FIG. 1 is illustrated in cross-section in further detail, and comprises a clamp 20, herein termed an alligator clamp for descriptive purposes. As seen in both FIGS. 1 and 2, the base portion 16 of alligator clamp 20 is integrally formed with opposing jaw portions 22 terminating in confronting rolled clamping ends 24 which provide the clamping action therebetween. The base and jaw portions 16 and 22 are formed of a spring material such as, for example, stainless steel, plastic, etc., configured such that the jaws are in a normally-closed condition. The ends 24 preferably are rolled to present smooth yet binding contact surfaces to the trailing ends of a suture thread 26 which is used to form the purse string suture (see FIGS. 3, 4A–4E and 5). A collapsible cylindrical member 28 formed, for example, of a soft deformable material such as soft plastic which is suitable for gripping the suture thread, is secured at one end to the base portion 16 and extends proximally therefrom past the clamping ends 24, terminating preferably in a diverging cone 30. The member 28 includes a lumen therethrough which is coaxial with the lumen formed by the coiled spring 10 configuration. A pair of grips 32 are pinned within respective rolled ends 24 and extend distally beyond the jaw and base portions 22 and 16, respectively, and provide means for spreading the jaw portions 22 when the grips 32 are pinched together such as with thumb and finger or forceps. As shown in FIG. 2, releasing of the pinching force on the grips 32 allows the jaw portions 22 and thus the ends 24 to clamp together, forcing the corresponding portions of the cylindrical member 28 inwardly against the suture thread 26 to lock the latter in place.

A suture-pulling needle 34 is utilized to install the clamping device in accordance with the invention, as more fully described in FIGS. 4A–4E. The needle has a length and outside diameter which allows the pertinent portion thereof to be inserted through the lumens in the cylindrical member 28, the spring 10 and the cap 12. Thus the pertinent portion of the needle 34 may be of the order of 0.060 inch (about 0.15 cm) with an overall needle length of four to ten inches (or 10.2 to 25.4 cm) to facilitate its manipulation by a surgeon. The needle 34 terminates at its distal end in a hooked tip 36 designed to engage and hook the trailing ends of the suture thread 26 when the hooked tip 36 is pushed beyond the cap 12. The engaged suture ends then are pulled through the clamping device by withdrawing the needle 34 from within the clamping device.

An optional feature which may be used with the clamping device of the present invention comprises a cannula clip 38 which is made of a spring-like band of material such as stainless steel, plastic, etc., formed in a generally semicircular shape. The clip 38 includes a post 40, one end of which is secured to or formed with, the band of material. The other end of the post 40 is secured to the cap 12 to extend generally radially therefrom. The optional cannula clip 38 provides means for aligning and attaching the clamping device to the cannula as the device is being threaded onto the trailing ends of the suture thread 26.

FIG. 3 shows a cross-section of, for example, an aorta 42 in which an incision has been made and an end of a cannula 44 has been inserted through the incision into the aorta. The cannula generally includes an annular ridge 46 extending radially outward to limit the extent of entry of the cannula into a heart or vessel; here the aorta 42. The clamping device of the invention is illustrated attached to a purse string suture 48, with the optional cannula clip 38 clipped to the cannula 44 above the annular ridge 46. It may be seen that the compressible sleeve means 8 of the clamping device, such as the compression spring 10, applies relatively constant, continuous tension to the purse string suture 48 to maintain the seal of aorta tissue about the cannula.

FIGS. 4A–4E illustrate several steps in the procedure of installing the clamping device on a purse string suture in accordance with the invention, for purposes of cannulation. By way of facilitating the description, the clamping device of the invention is illustrated in FIGS. 4A–4E and 5 as formed of the compressible sleeve means 8 and the alligator clamp 20. However, any combination of compressible sleeve means such as the compression spring 10, or the compressible elastomeric or nitinol, etc., sleeve of description below may be combined with the various clamp mechanisms 18 exemplified herein.

More particularly, FIG. 4A illustrates the construction of a purse string suture 48 about a cannula 44 inserted in an incision, for example, in the aorta. The trailing ends of the suture thread 26, including a suture needle 50, extend a selected length from the purse string suture. The suture needle 50 is then cut off. In the next step, depicted in FIG. 4B, a surgeon pinches the grips 32 together to open the clamp mechanism 18, and the suture-pulling needle 34 is inserted through the coaxial lumens of the cylindrical member 28, the compressible sleeve means 8 (such as the compression spring 10) and the cap 12 until the hooked tip 36 protrudes a short distance therefrom. The surgeon then hooks the trailing ends of the suture thread 26 into the hooked tip 36 of the needle 34 to firmly grasp the trailing ends, as shown at 52. The trailing ends should be sufficiently long to allow the hooked tip 36 subsequently to be pulled completely through the clamping device.

FIG. 4C depicts the step of withdrawing the suture-pulling needle 34 from the clamping device as shown by arrow 53 to expose the hooked tip 36 and the trailing ends of the suture thread 26. During this step the grips 32 are pinched together to open the clamp mechanism 18 so that the needle 34 and trailing ends can be pulled through the clamping device. The cannula clip 38 (if provided) is clipped onto the cannula 44, and the suture-pulling needle 34 is disengaged from the ends of the suture thread 26.

In the next step depicted in FIG. 4D, the trailing ends of the suture thread 26 preferably are grasped by a surgeon between thumb and finger and pulled (see arrow 55) to apply a firm tension force to the purse string suture while maintaining the trailing ends taut. The grips 32 are grasped by the jaws of forceps 54 (or between thumb and finger) and are pinched together as shown by arrows 56 to open the confronting ends 24 of the alligator clamp 20, that is, the clamp mechanism 18, to remove the contact of the cylindrical member 28 against the suture thread 26. Simultaneously with the application of the pinching force on the grips 32, an axial force depicted by arrow 58 is provided opposite in direction to the force 55, by urging the forceps and thus the clamp mechanism 18 towards the cannula 44 against the force produced by compression of the compressible sleeve means 8. When the compressible sleeve means 8 is appropriately compressed, that is, compressed sufficiently to provide the tension desired by the surgeon on the purse string suture, the forceps are opened to allow the jaws 22 to close. This clamps the ends 24 together to deform the pertinent portion of the cylindrical member 28 against the suture thread 26 to lock the latter in place.

FIG. 4E illustrates the clamping device of the invention installed on a purse string suture 48 which provides a seal about a cannula 44 due to the continuous and precalibrated tension applied to the purse string suture via the compressible sleeve means 8. As may be seen, the invention has a low profile and does not require extended sleeves and forceps to maintain the purse string suture in place. In addition, the clamping device of the invention insures a continuously applied, relatively constant and predetermined amount of tension on the purse string suture to prevent the seal about the cannula from deteriorating.

As depicted in FIG. 5, upon the completion of surgery and/or when removal of the clamping device is desired, a surgeon may employ the forceps 54, or thumb and finger, to again pinch the grips 32 of the alligator clamp 20 to release the clamping action thereof on the trailing ends of the suture thread 26. The cannula clip 38 is unclipped from the cannula 44 and the clamping device is removed from the purse string suture 48 by movement of the forceps 54 and clamping device away from the cannula 44, as depicted by arrow 59, as the compressible sleeve means 8 decompresses.

Figure 6:
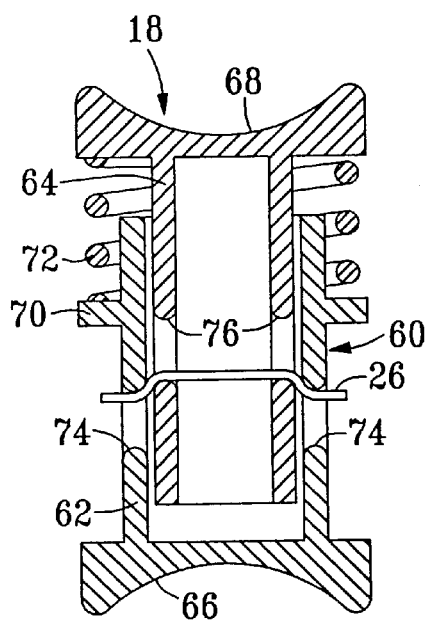
FIGS. 6 and 7 are cross-sectional views illustrating alternative embodiments of clamp mechanisms of the present invention.

FIG. 6 illustrates in cross-section an alternative embodiment of the clamp mechanism 18 which may be employed in the clamping device of the invention in place of the alligator clamp 20 of the previous figures. More particularly, FIG. 6 illustrates a cylinder clamp 60 comprising preferably an outer cylindrical member 62 and a coaxial inner sleeve 64 translatable within the member 62. The opposite ends of the member 62 and sleeve 64 terminate in caps of larger respective diameters, which further include respective depressions or grooves 66 and 68 formed therein to allow the clamp 60 to be readily grasped and manipulated by thumb and finger or forceps in the manner described in FIGS. 4B–4D and 5. An annular shoulder 70 is formed about the outer member 62 to provide means for confining a compression spring 72 between the shoulder 70 and a confronting shoulder of the cap of the inner sleeve 64. The member 62 and sleeve 64 each include diametrically opposed holes 74, 76 respectively, which are arranged to be axially aligned with all four holes in register when the member 62 and sleeve 64 are pinched together to compress the spring 72, and which are not aligned or in register when the pinching action is released.

The cylinder clamp 60 is solidly secured to the proximal end of a compressible sleeve means such as the compression spring 10 of the previous FIG. 1, with the lumen of the compression spring 10 coaxially aligned with the holes 74 in the outer cylindrical member 62. Thus, the arrangement of a compressible sleeve means 8 and the clamp mechanism 18 is similar in both of the clamping devices of FIGS. 1–5 and 6. In the embodiment of FIG. 6, the cylinder clamp 60 is pinched to align the holes 74, 76 to allow the trailing ends of the suture thread 26 to be pulled through the clamping device via the suture-pulling needle 34 and then locked in place on the cannula 44, in the manner described in FIGS. 4A–4E. The device is removable with the same procedure described relative to FIG. 5.

Figure 7:
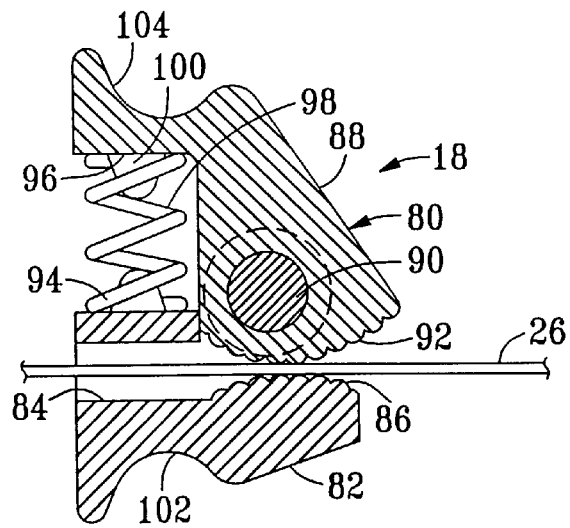

FIG. 7 illustrates in cross-section another alternative embodiment of the clamp mechanism 18 which may be used in combination with a compressible sleeve means 8, such as the compression spring 10, in place of the alligator clamp 20 or the cylinder clamp 60. To this end, FIG. 7 illustrates a cam-lock clamp 80 which includes a support member 82 having a central bore 84 therethrough terminating at the proximal ends thereof in a raised series of teeth 86. A cam member 88 is pivotally secured to the support member 82 via a pin 90, and includes an arcuate cam surface having a series of teeth 92 confronting the raised series of teeth 86. In typical cam fashion, pivoting of the cam member 88 about the pin 90 increases and decreases the space between the confronting teeth 86 and 92, thereby allowing the trailing ends of the suture thread 26 to be pulled through the clamp 80 or to be clamped firmly between the confronting series of teeth 86 and 92.

The support member 82 and cam member 88 include facing ledges 94 and 96, respectively, configured to confine therebetween a compression spring 98. Nubs or pegs 100 are formed on the ledges to maintain the containment of the spring 98. The opposite outer surfaces of the support member 82 and cam member 88 include respective depressions or grooves 102 and 104 formed therein, which allow the clamp 80 to be readily grasped and manipulated by thumb and finger or by forceps in the manner described in FIGS. 4B–4D and 5.

As in the embodiments of FIGS. 1–5 and FIG. 6, the cam-lock clamp 80 of FIG. 7 is solidly secured to the proximal end of a compressible sleeve means 8, with the central bore 84 in coaxial alignment with the lumen of the sleeve means. A pinching force applied to the grooves 102, 104 compresses the spring 98 and opens the cam-lock clamp 80, and release of the pinching force allows the spring 98 to clamp the series of teeth 86, 92 together to lock therebetween the trailing ends of the suture thread 26.

FIG. 8 illustrates an alternative embodiment 108 of the suture-pulling needle 34 of FIGS. 1, 4B, 4C. More particularly, the distal end of the needle 108 has secured thereto a suture-pulling wire snare 110 formed of thin spring wire in the shape of a flattened diamond. The snare 110 is similar to the spring wire configuration of a sewing needle threader. The distal tip 112 of the snare 110 converges sharply to provide a wedging action, whereby the trailing ends of the suture thread 26 are securely held due to the wedging action and the pinching of the sides of the snare by the sleeve means 8 and clamp mechanism 18 as the needle 108 is withdrawn therefrom in the manner described relative to FIG. 4C.

FIGS. 9A and 9B illustrate an alternative embodiment 114 of the compressible sleeve means 8 of the previous figures. The compressible sleeve or tube illustrated in FIGS. 4B–4E and 5 here comprises a tube formed, for example, of a compressible material such as nitinol, an elastomeric material, etc., secured at its proximal end to a clamp mechanism 18 such as illustrated in FIGS. 2, 6, 7. As depicted in FIG. 9A, the tube has a predetermined number and width of slots 116 selectively formed in the length thereof, to provide a similar number of strips 118 of sleeve material. Thus, when the clamp mechanism 18 is forced towards the sleeve 114 (arrow 120) while holding the suture thread 26 taut (arrow 122) as described with respect to FIG. 4D, the strips 118 buckle radially outward as shown in FIG. 9B. This in turn applies the continuous and precalibrated tension of previous discussion on the purse string suture.

Although the clamping devices of, for example, FIGS. 1, 2, 6, 7 and 9 are described herein with specific elements and configurations by way of illustration, it is to be understood that various modifications thereto may be practiced without departing from the spirit and scope of the invention. To illustrate, the members 62, 64 of FIG. 6 may be square, rectangular, oval, etc., in cross-section rather than cylindrical. Likewise, in FIGS. 6 and 7 the cylindrical compression springs 72 and 98 may be replaced by leaf springs or the like, and/or the compression spring 10 may be a ribbon or helical spring with a lumen therethrough, rather than cylindrical as described herein. Furthermore, the compressible sleeve means 8 may be a compressible smooth, slotted or corrugated elastomeric, polymer, nitinol, etc., tube or lumen, or other equivalent compressible member, structure and/or material which is capable of applying a tension force on the purse string suture when confined thereagainst by a compression means such as the clamp mechanisms illustrated herein.

Thus, the scope of the present invention is defined by the following claims and their equivalents.

What is claimed is:

1. Apparatus for securing a purse string suture in place, the purse string suture having trailing ends extending therefrom, comprising:

spring means confining therein the trailing ends and abutting the purse string suture at a distal end of the spring means; and clamp means secured to the spring means at a proximal end of the spring means and adapted to receive and clamp the trailing ends therein when the spring means is compressed between the purse string suture and the clamp means.

2. The apparatus of claim 1 wherein:

the spring means comprises an elongate compression spring confining therein the trailing ends; and the clamp means is threaded along with the spring means over the trailing ends when the clamp means is open and is clamped to the trailing ends to confine the spring means when the spring means is compressed against the purse string suture.

3. The apparatus of claim 2 wherein the clamp means comprises an alligator clamp.

4. The apparatus of claim 3 wherein the alligator clamp comprises:

confronting jaw members disposed to be normally closed; and means secured to the jaw members for opening the jaw members to enable threading the compression spring and alligator clamp over the trailing ends, wherein release of the opening means locks the trailing ends in the alligator clamp.

5. The apparatus of claim 2 wherein the clamp means comprises a cylinder clamp.

6. The apparatus of claim 5 wherein the cylinder clamp comprises:

a hollow member having oppositely arranged holes therein;

a second member slidably disposed within the hollow member and having a hole therein which aligns with the holes in the hollow member; and a spring confined between the hollow member and the second member for maintaining mis-alignment of the holes in the hollow member with respect to the hole in the second member to secure the trailing ends therebetween.

7. The apparatus of claim 2 wherein the clamp means comprises a cam-lock clamp.

8. The apparatus of claim 7 wherein the cam-lock clamp comprises:

a support member having a bore therein and including a first suture contacting means;

a cam member pivotally secured to the support member and having a second suture contacting means; and a spring confined between the support member and the cam member for urging the first suture contacting means against the second suture contacting means to secure the trailing ends therebetween.

9. The apparatus of claim 2 wherein the purse string suture is disposed to seal a cannula in place, including:

clip means secured to the distal end of the spring means for detachably securing the apparatus to the cannula prior to compression of the spring means against the purse string suture.

10. The apparatus of claim 1 wherein:

the spring means comprises compressible sleeve means confining therein the trailing ends; and said clamp means being secured to the proximal end of the compressible sleeve means.

11. The apparatus of claim 10 wherein the compressible sleeve means is formed of a compressible elastomeric tube or lumen.

12. The apparatus of claim 10 wherein the compressible sleeve means comprises:

a tube of compressible material;

said tube having a selected plurality of slots formed in the length thereof to form thereby a plurality of strips; and said strips buckling radially outward when the tube is axially compressed to apply tension on the purse string suture.

13. Apparatus for securing a purse string suture around a cannula or catheter placed in a tissue structure, the purse string suture having trailing ends extending therefrom, comprising:

elongate compressible sleeve means having a distal and a proximal end;

clamp means secured to the proximal end of the sleeve means;

said sleeve means and said clamp means having a common lumen therethrough;

threading means adapted to extend through the common lumen for threading the trailing ends through the sleeve means and clamp means; and means for compressing the sleeve means while simultaneously clamping the clamp means on the trailing ends to confine the distal end of the compressed sleeve means against the purse string suture.

14. The apparatus of claim 13 wherein the means for compressing includes:

means for grasping the clamp means and for applying a force against the sleeve means to compress same against the purse string suture.

15. The apparatus of claim 14 wherein the cannulation is to be disassembled, wherein the means for grasping releases the clamp means and decompresses the sleeve means to allow unthreading the trailing ends therefrom.

16. A method for securing a purse string suture in place, the purse string suture being formed of a suture thread having trailing ends extending from the purse string suture, comprising the steps of:

threading the trailing ends of the suture thread through a compressible sleeve;

applying a force against a proximal end of the compressible sleeve to compress the sleeve and urge a distal end thereof against the purse string suture; and clamping the trailing ends of the suture thread at the proximal end of the compressed sleeve to maintain tension on the purse string suture.

17. The method of claim 16 wherein the step of threading includes:

hooking the trailing ends of the suture thread via a suture-pulling needle; and pulling the hooked trailing ends through the sleeve to enable the step of clamping.

18. The method of claim 16 wherein the step of clamping includes:

attaching a clamping means to the trailing ends of the suture thread at the proximal end of the sleeve after performing the step of applying a force.

19. The method of claim 18 wherein the step of applying a force includes:

grasping the clamping means to open same; and forcing the clamping means against the proximal end of the sleeve to compress the latter.

20. A device for securing a purse string suture, comprising:

a sleeve having distal and proximal ends and defining a longitudinal axis therebetween for receiving trailing ends of the purse string suture, wherein said sleeve is compressible along said longitudinal axis; and compression means integral with said proximal end of said sleeve for compressing said sleeve along said longitudinal axis when said sleeve is operatively positioned over said trailing ends.

21. The device of claim 20 wherein:

said sleeve comprises a compressible elastomeric tube or lumen; and said compression means includes means secured to the proximal end of the compressible tube or lumen for maintaining the tube or lumen in said compressed state.

22. The device of claim 20 wherein:

said sleeve comprises a compressible spring means; and said compression means includes means secured to the proximal end of the compressible spring means for maintaining the spring means in said compressed state.

23. The device of claim 20 wherein:

said compression means includes clamp means secured to the proximal end of the sleeve for clamping onto the trailing ends to maintain the sleeve in said compressed state.

* * * * *